(12) United States Patent
Winter et al.

(10) Patent No.: US 7,819,008 B2
(45) Date of Patent: Oct. 26, 2010

(54) METHOD OF INSPECTING CANOPY STRUCTURES

(75) Inventors: Neil S. Winter, Aiken, SC (US); D. Eric Wilson, Aiken, SC (US)

(73) Assignee: Canopex, Inc., Aiken, SC (US)

( * ) Notice: Subject to any disclaimer, the term of this patent is extended or adjusted under 35 U.S.C. 154(b) by 1044 days.

(21) Appl. No.: 11/483,841

(22) Filed: Jul. 10, 2006

(65) Prior Publication Data

US 2008/0006087 A1     Jan. 10, 2008

(51) Int. Cl.
    *G01H 1/00* (2006.01)
(52) U.S. Cl. .......................................... 73/584; 702/33
(58) Field of Classification Search .................. 73/584; 356/3.02, 3.03; 702/34, 35, 39, 40, 155, 702/158, 159, 166, 170, 171
    See application file for complete search history.

(56) References Cited

U.S. PATENT DOCUMENTS 4,779,453 A * 10/1988 Hopenfeld .................. 73/86
4,922,748 A * 5/1990 Hopenfeld .................. 73/86
5,118,464 A * 6/1992 Richardson et al. ......... 376/252
5,804,730 A * 9/1998 Pfannenstiel et al. ......... 73/622
6,327,921 B1 * 12/2001 Hsu et al. .................. 73/866.5
6,880,379 B2 * 4/2005 Hedberg et al. ............. 73/12.01
7,331,217 B2 * 2/2008 O'Sullivan .................. 73/49.1
7,580,800 B1 * 8/2009 Winter et al. ................ 702/33
2006/0243051 A1* 11/2006 Bui et al. ..................... 73/618
2007/0056374 A1* 3/2007 Andrews ...................... 73/628
2008/0226122 A1* 9/2008 Thompson et al. ........... 382/100

OTHER PUBLICATIONS

"Canopex the Canopy Experts", Canopy Inspections, 2006. http://www.TheCanopyExperts.com.*

* cited by examiner

*Primary Examiner*—Hezron Williams
*Assistant Examiner*—Samir M Shah
(74) *Attorney, Agent, or Firm*—Michael A. Mann; Nexsen Pruet, LLC

(57) ABSTRACT

A method of inspecting canopy structures is provided to determine the structural integrity of the roof support system. The method includes steps designed to uncover hidden deficiencies in the roof support system through nondestructive testing and discovery. Timely use of the method of inspection not only minimizes the risk of canopy collapse but also produces information needed for making repair or replacement of the roof support system.

15 Claims, 17 Drawing Sheets

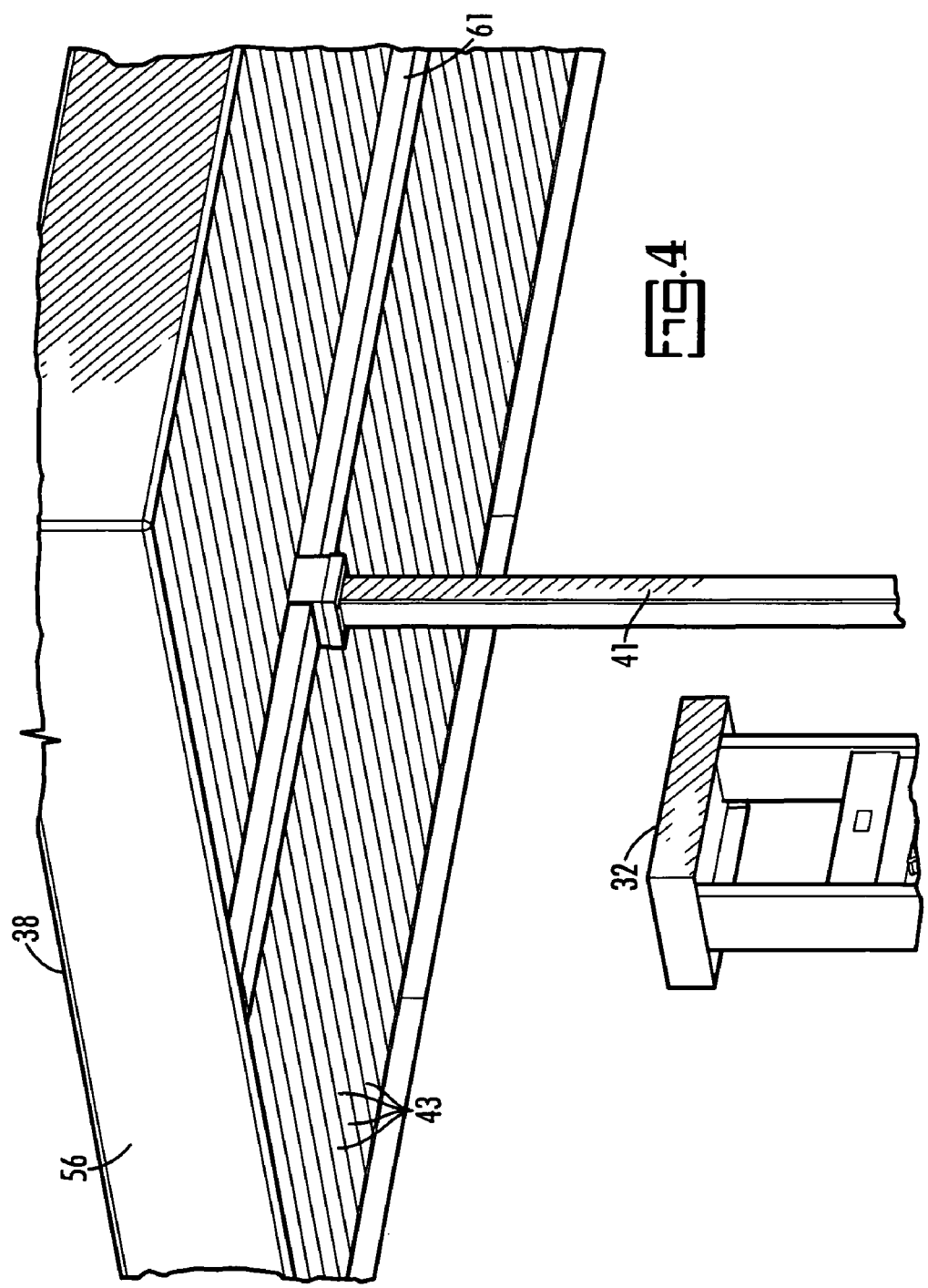

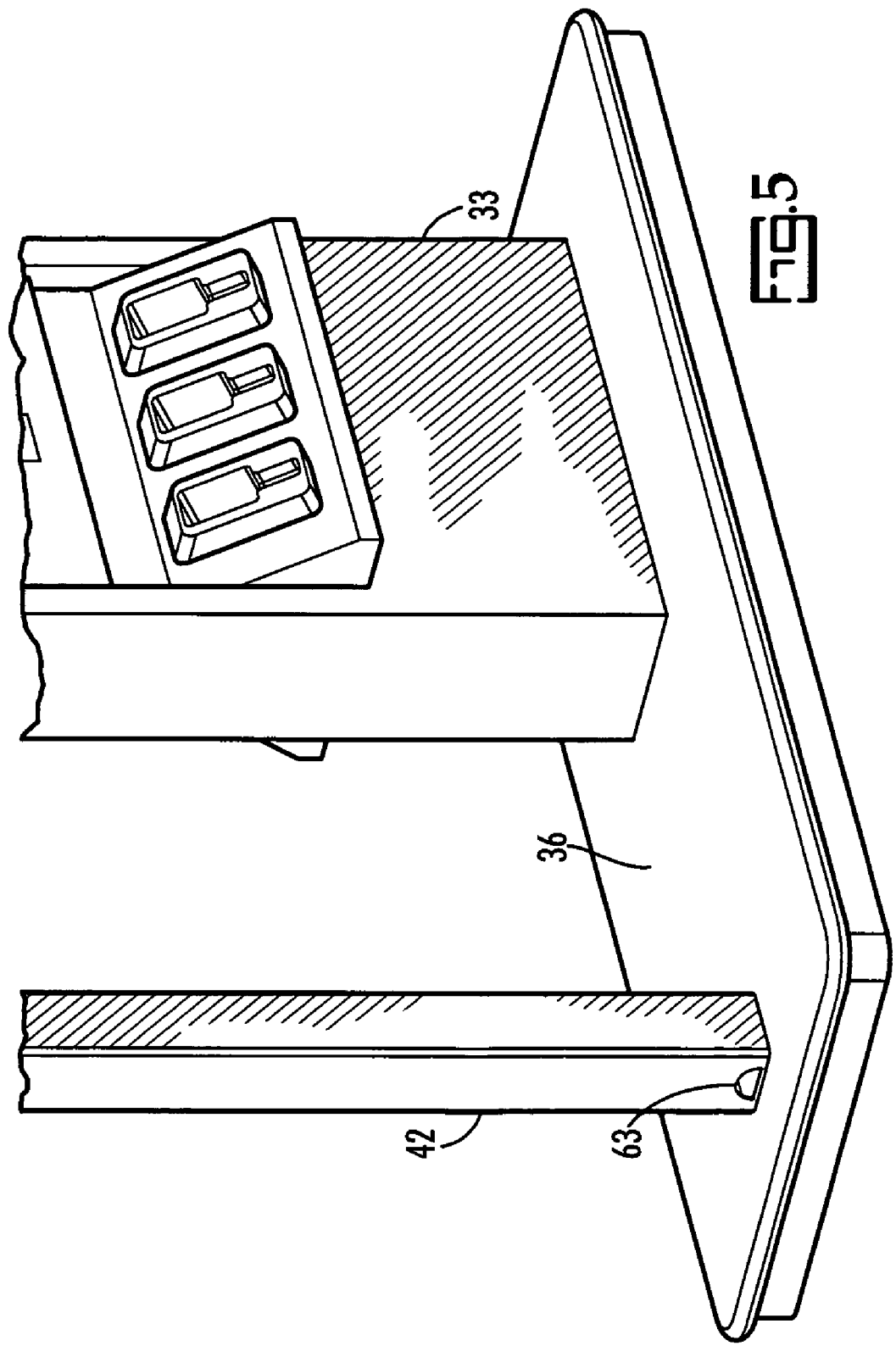

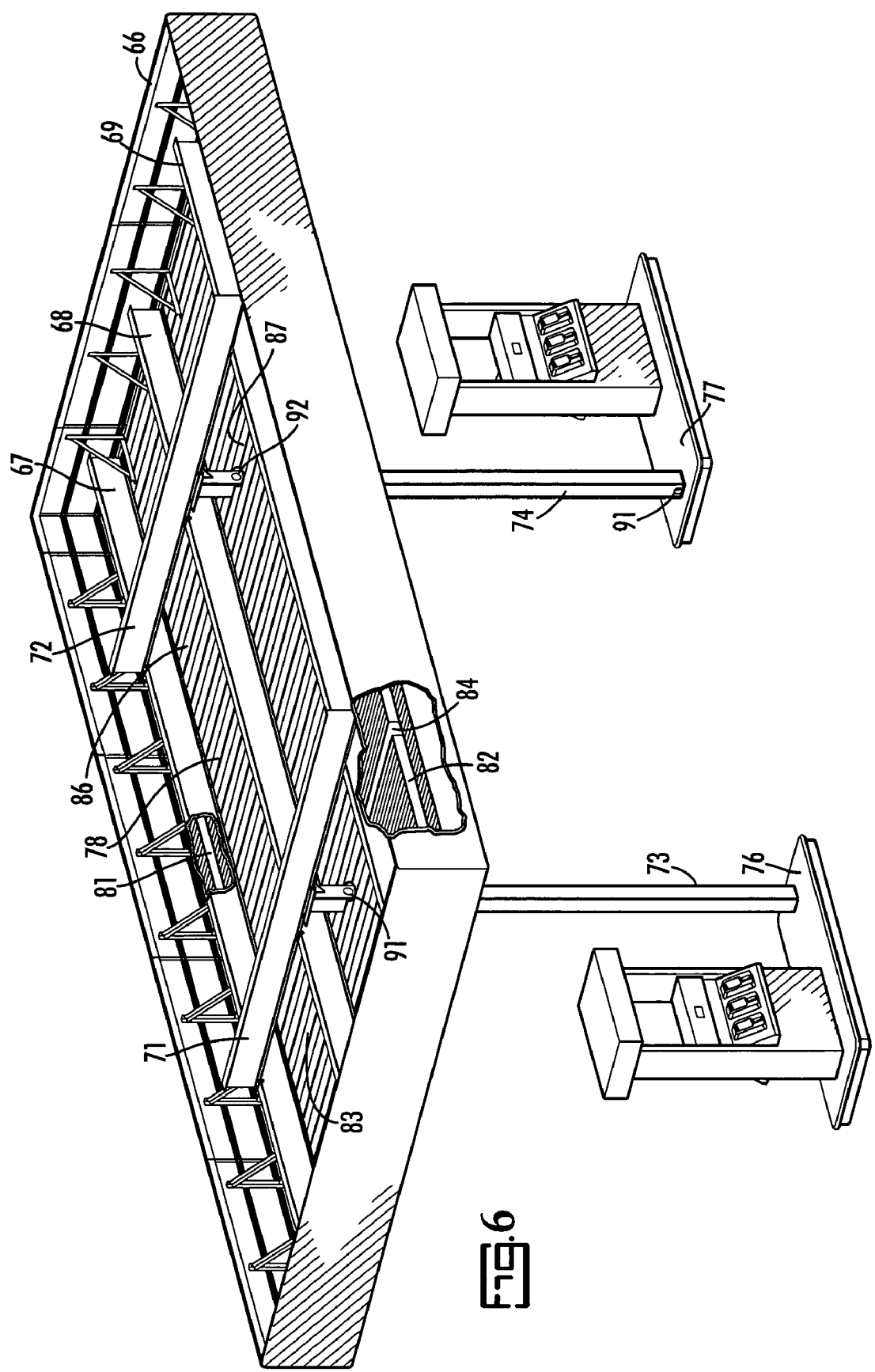

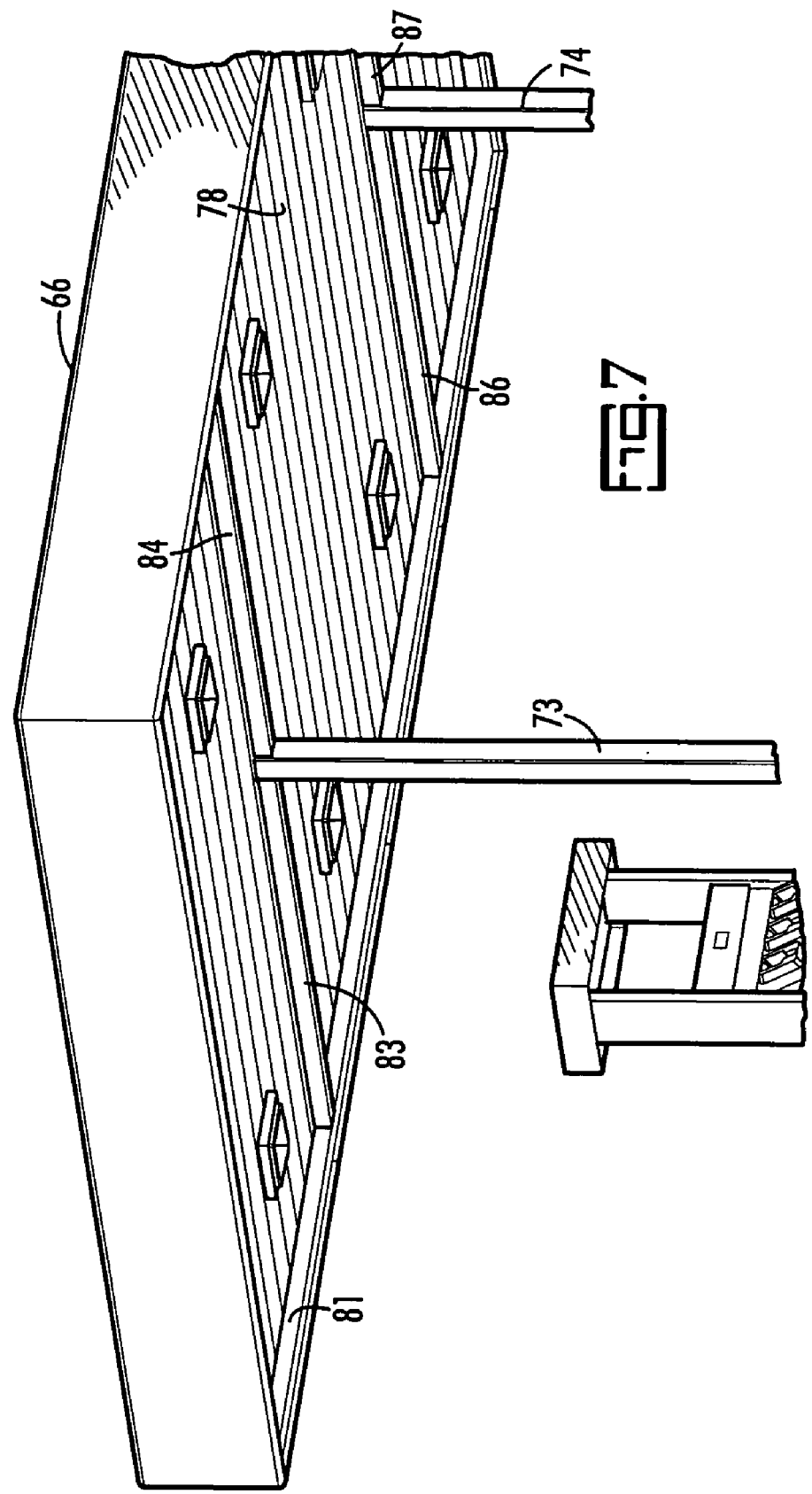

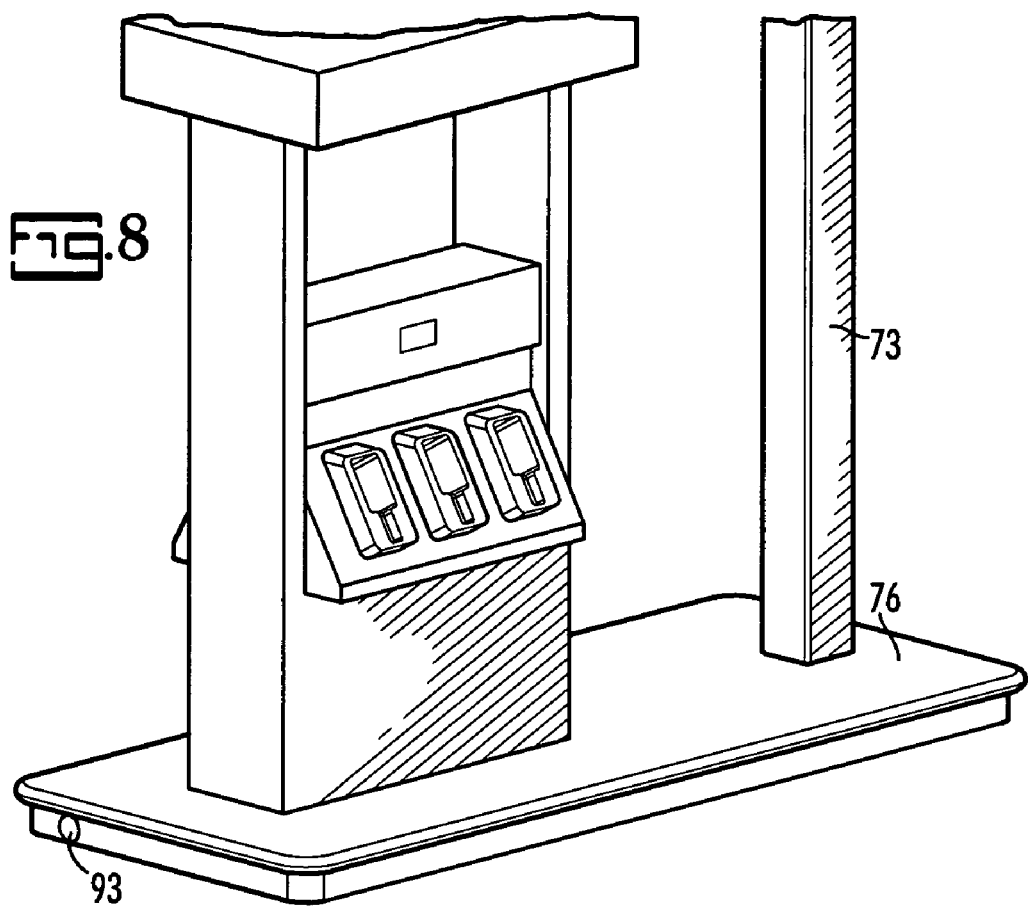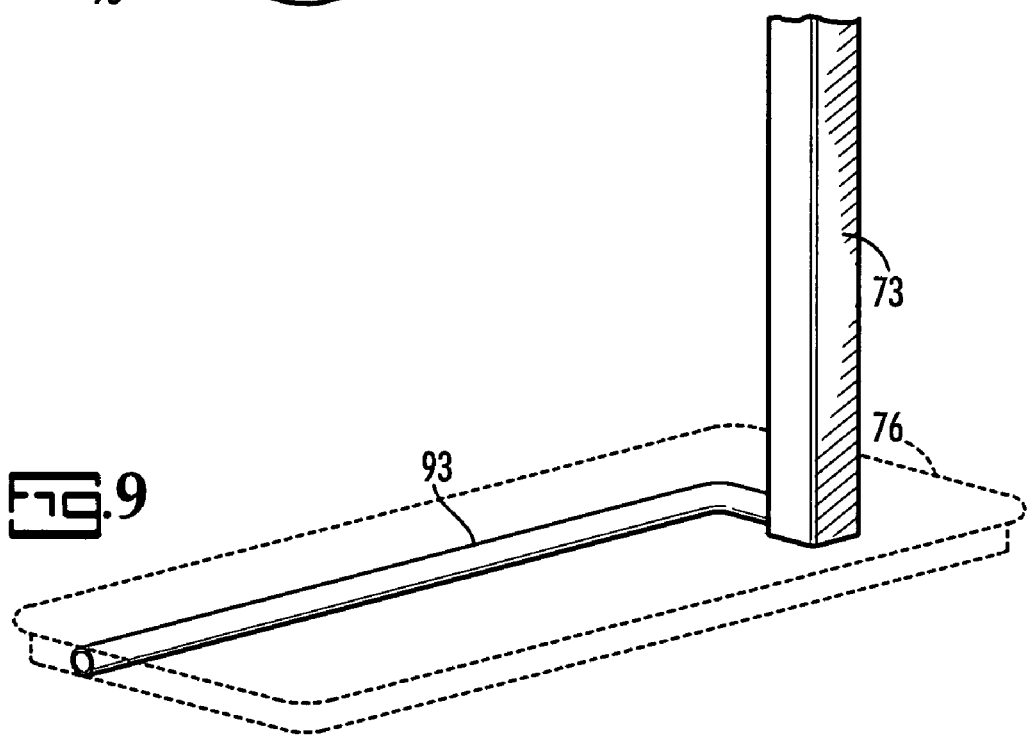

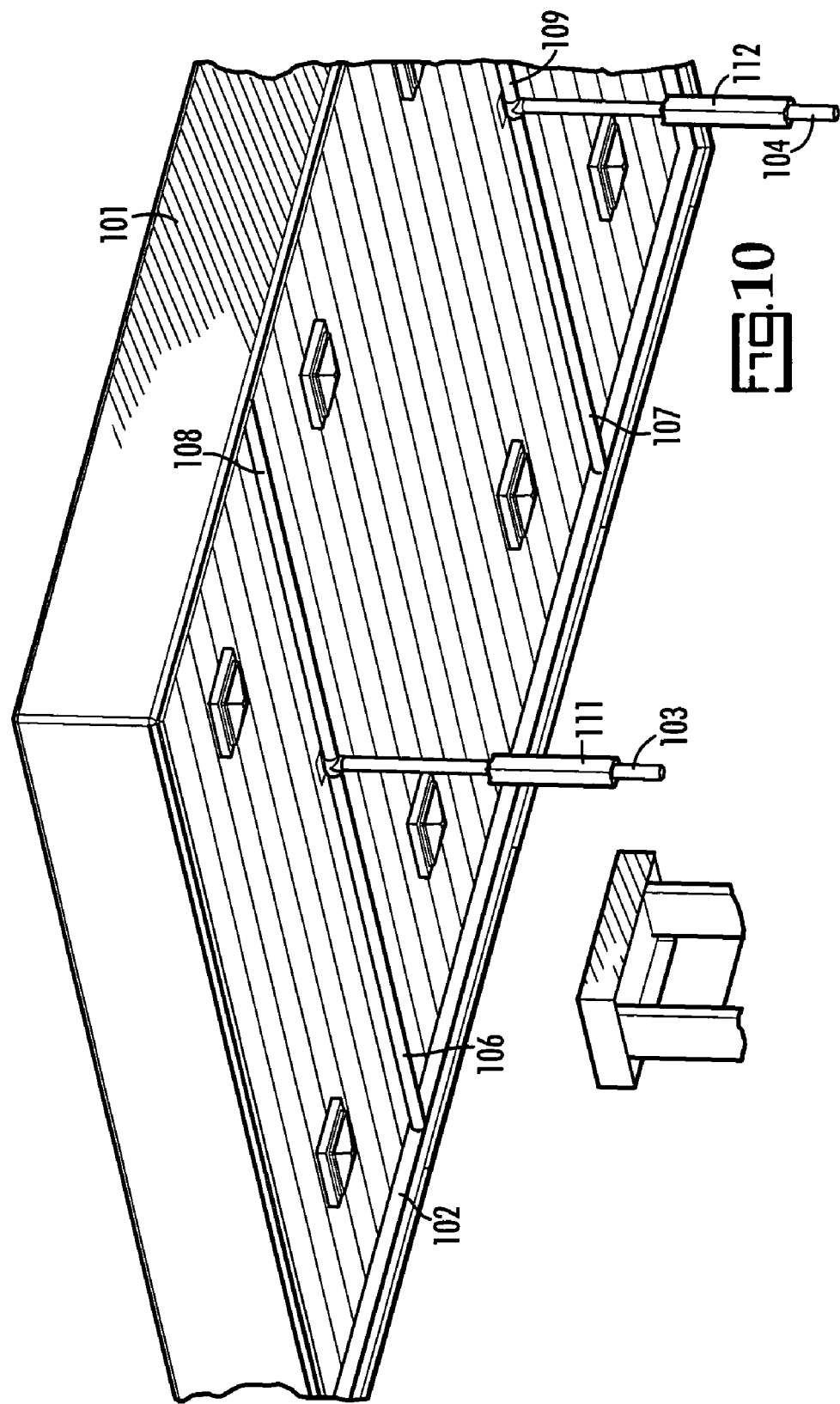

METHOD OF INSPECTING CANOPY STRUCTURES

BACKGROUND OF THE INVENTION

Canopy structures such as installed at vehicle fuel dispensing service stations typically have flat roofs supported by hollow vertical columns made of corrodible material such as steel. Such columns are often used as conduits for draining water from the flat roof, thus exposing the interior of the columns to corrosive deterioration and loss of strength needed to support the roof. Since the deterioration of the columns may be entirely internal, they can weaken to a dangerous condition resulting in a collapse of the canopy without the owner or operating personnel being aware of their dangerously weakened condition.

SUMMARY OF THE INVENTION

This invention provides a method of non-destructively inspecting canopy structures to determine their structural integrity and also to identify inadequacies or defects in the roof water drainage system. The method of inspection includes visual inspection to identify areas of deterioration or concern, impact and resonance testing of vertical support columns checking support column thickness using ultrasonic technology and may optionally also include inspection of the drainage system using fiber optic technology such as a fiberscope. Several methods of inspection are herein disclosed for a variety of canopy structures.

BRIEF DESCRIPTION OF THE DRAWINGS

The accompanying drawings illustrate typical canopy structures and steps in methods of inspecting such structure, in which:

FIG. 4 is a perspective view of part of the underside of the canopy illustrated in FIGS. 1, 2 and 3;

FIG. 5 shows a drain opening in the lower end of a canopy support column mounted on a fuel dispensing island of a vehicle service station;

FIG. 6 is a top perspective view of a second vehicle fuel service station canopy having gutters at laterally opposite sides of the roof which drain to two support column through lateral gutters;

FIG. 7 is a perspective view of the canopy of FIG. 6 showing part of the underside of the roof, the gutters and the support columns;

FIG. 8 shows the lower part of a canopy support column and a fuel dispensing island with a drain discharge opening;

FIG. 9 shows the conduit in the island of FIG. 8 interconnecting the drain opening and the lower end of the support column;

FIG. 10 is a perspective view of the underside of part of a third canopy construction, similar to that of FIGS. 6 and 7, in which the gutters at the laterally opposite sides of the roof are drained by piping;

DETAILED DESCRIPTION OF THE INVENTION

Figure 1:
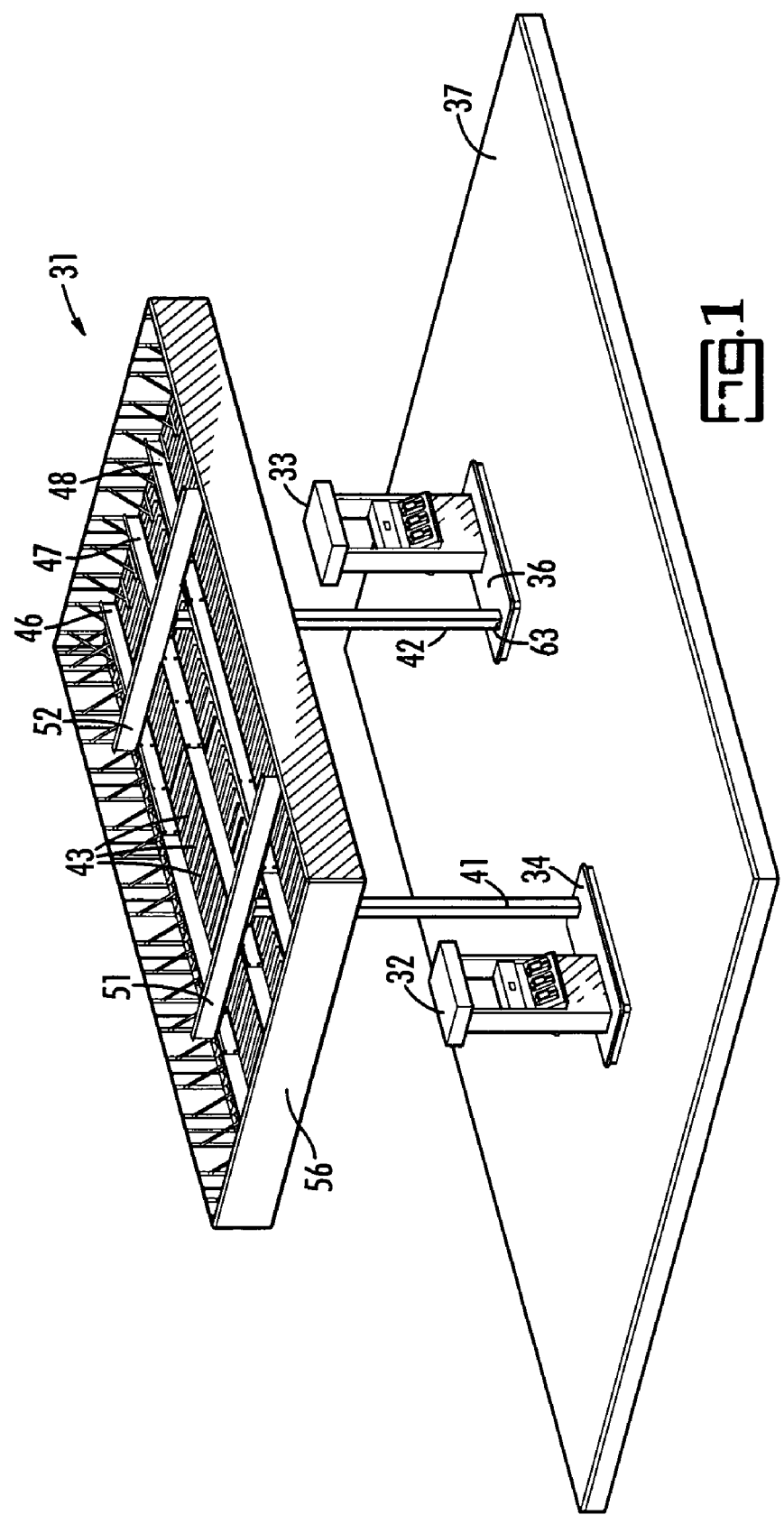
FIG. 1 is a perspective view of a first vehicle fuel servicing station canopy having a roof with a single central longitudinal gutter and two support columns which serve as drainage conduits.
Figure 2:
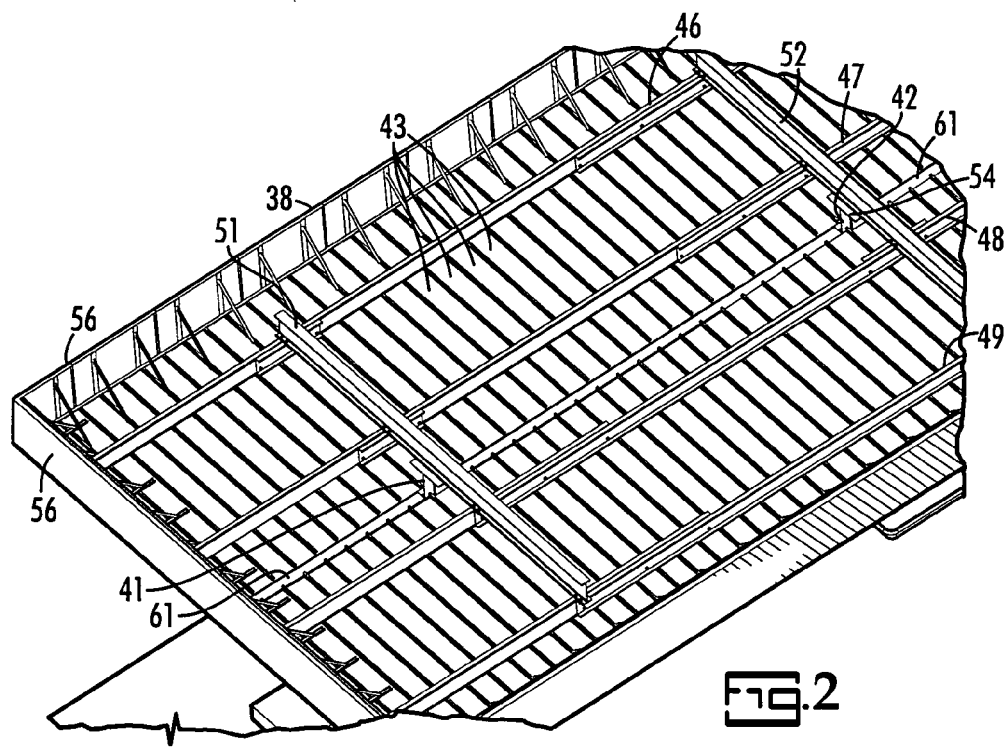
FIG. 2 is a top perspective view of part of the roof of the canopy shown in FIG. 1.
Figure 3:
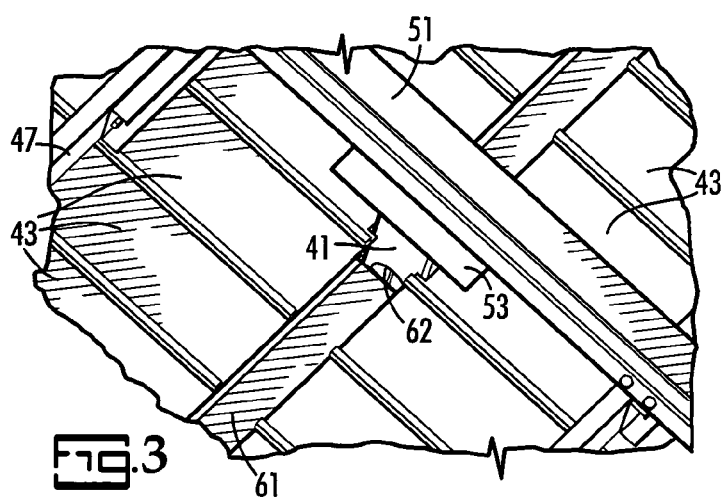
FIG. 3 is an enlarged top perspective view of part of the canopy roof showing an opening in a support column through which the central gutter drains.

FIGS. 1 through 12 illustrate several types of vehicle fuel service station canopies to which the herein described methods of inspection can be beneficially applied. FIGS. 1, 2, 3, 4 and 5 show one type of canopy for a vehicle fuel service 31 station to which the herein disclosed method of inspection is advantageously applied. The service station includes a pair of fuel dispensing unit or modules 32, 33 mounted on concrete service islands 34, 36, respectively, which in turn are mounted on a concrete floor 37. The canopy 31 includes an elongated roof 38 supported on a pair of upright or vertical hollow steel columns 41, 42 of square or quadrilateral cross section the lower ends of which are embedded in and supported by the islands 34, 36 respectively. The roof 38 includes interconnected roof panels 43 secured to the underside of longitudinally extending horizontal steel roof stringers or channels 46, 47, 48, 49. The vertical support columns 41, 42 support a pair of steel I beams 51, 52 which in turn support the roof stringers 46, 47, 48, 49. The I beams 51, 52 rest on horizontal steel plates 53, 54 which seal off the top of the columns 41, 42. A façade 56 rims the roof 38. Water on the roof 38 drains into a central gutter 61 which in turn drains into the support columns 41, 42 through openings. One such opening 62 is shown in FIG. 3, their opposite sides facing the gutter 61. Water is discharged from the columns 41, 42 through openings 63 at their bottoms, only one of which is shown.

A second type vehicle fuel service station canopy 66 is illustrated in FIGS. 6 and 7. The canopy 66 includes three longitudinal roof stringers 67, 68, 69 supported by two transverse I beams 71, 72. The I beams 71, 72 are supported on hollow vertical steel columns 73, 74 mounted on fuel dispensing islands 76, 77. The roof 78 of the canopy 66 includes a pair of longitudinally extending gutters 81, 82 at its laterally opposite sides which drain to the support columns 73, 74 by way of laterally extending connecting gutters 83, 84, 86, 87. Openings 91, 92 are formed in opposite sides of the support columns 73, 74, respectively, for draining the water from the roof 78 via the connecting gutters 83, 84, 86 87. An opening 91 at the bottom of column 74 allows discharge of water from its interior. A similar opening, not shown is provided in column 73.

FIGS. 8 and 9 show an alternative discharge of water from the column 73 through a conduit 93 embedded in the island. In some service stations the canopy water is discharged from the support column underground with or without a storm sewer connection. Debris or other obstruction in such underground discharge systems can result in a back up of water in the steel support column with attendant corrosion or rusting of the column.

Figure 11:
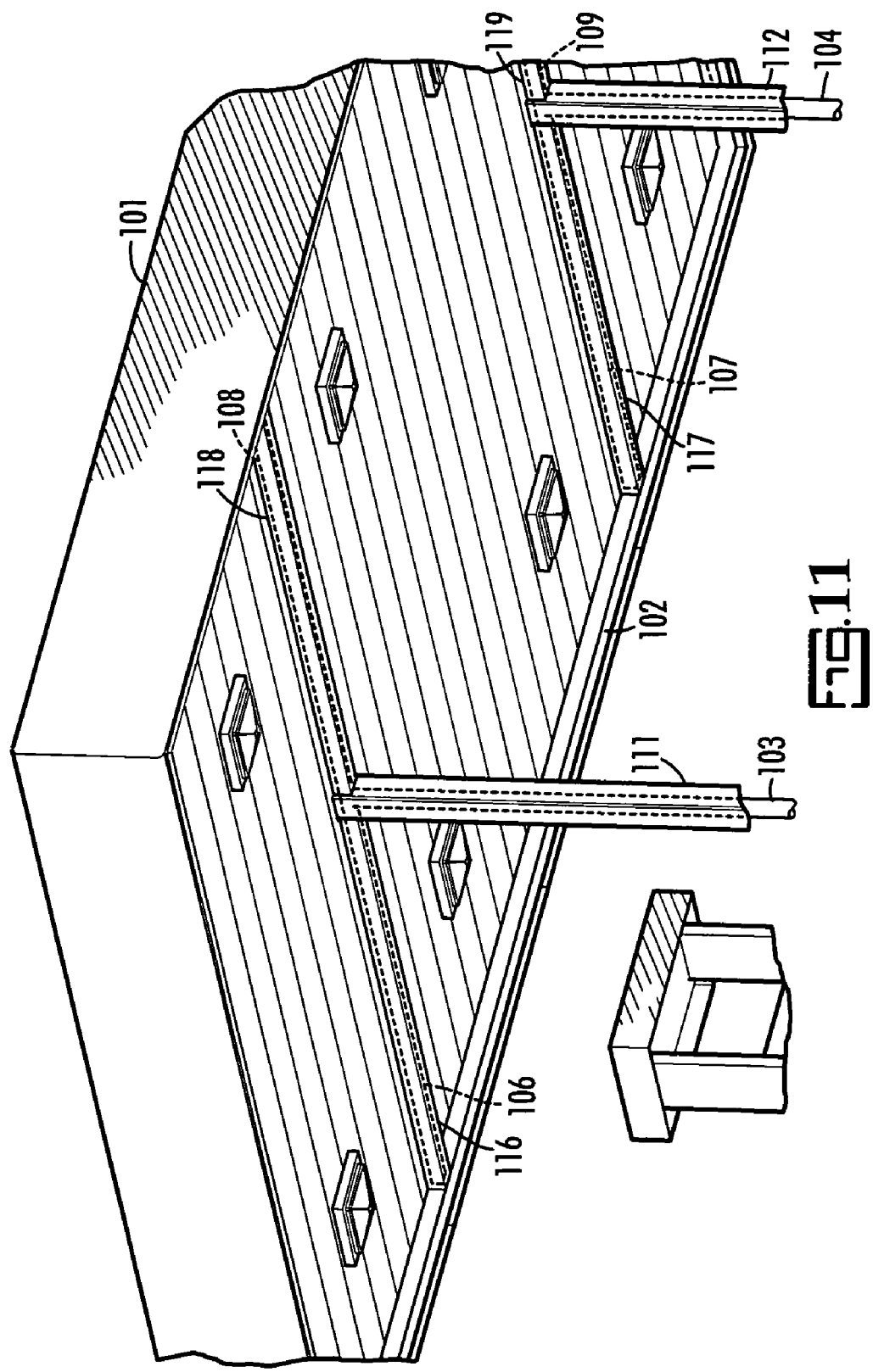
FIG. 11 is a perspective view similar to FIG. 10 showing the piping between the laterally opposite gutters and the support columns boxed in for decorative purposes.
Figure 12:
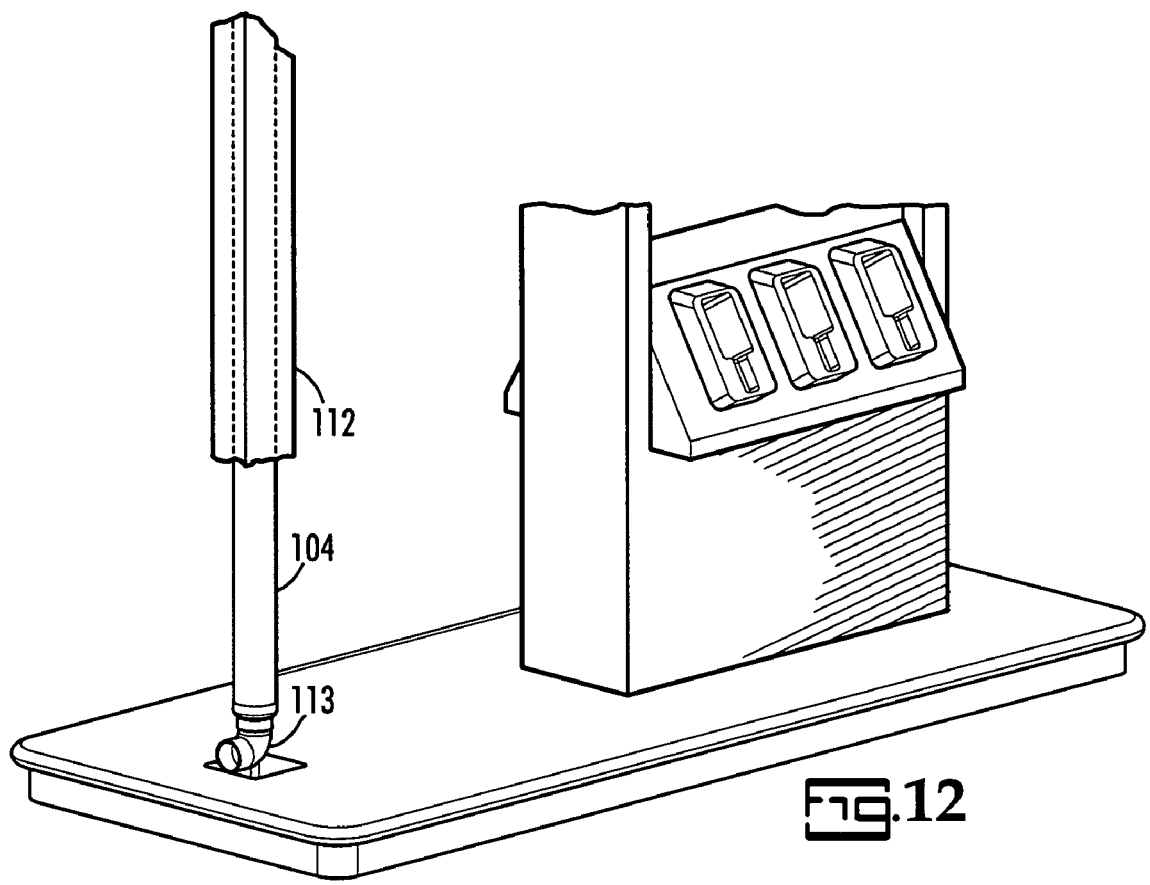
FIG. 12 shows a drain discharge from the piping of FIGS. 10 and 11.

FIG. 10 illustrates a canopy 101 having gutters at laterally opposite sides, only gutter 102 of which is shown, which are interconnected to vertically disposed PVC pipes 103, 104 by laterally extending PVC pipes 106, 107, 108, 109. The pipes 106, 107 extend downwardly through the support columns 111, 112 and, as shown in FIG. 12, water is discharged from the lower end of the columns, in FIG. 12 shows a discharge elbow 113 at the lower end of the conduit 104. An opening not shown is provided in the support column 112 to allow discharge of water from the elbow 113. In a similar manner, water is discharged from the conduit 103 through an opening at the lower end of the support column 111. FIG. 11 shows a construction similar to that of FIG. 10; however, the lateral pipes 106, 107, 108, and 109 are boxed in with trough shaped members 116, 117, 118, 119 to improve the ceiling décor.

When the unprotected interior of the hollow steel support columns 41, 42, 73, 74, 111, 112 is exposed to moisture they will rust. The extent of the interior rust is hidden from view and thus the owner and operating personnel of the service station are not aware of the weakened condition of the support columns. Canopies have collapsed because of structural failure of the support columns due to excessive rust deterioration. The collapse of a canopy can be catastrophic with possible personal injury, property damage and fire. The herein disclosed inspection method reveals the location and extent of deterioration in the canopy support structure, thereby affording the owner and operating personnel the opportunity to take corrective action in a timely manner. Periodic inspections conducted according to the herein disclosed methods and timely corrective action minimizes risk of collapse of the canopy.

The method of inspection includes testing procedures which are designated to not interfere with normal operation of the service facility. Traffic flow and customer access to the fueling modules is not interrupted. Preferably a sketch showing a plan view of the canopy is developed showing critical dimensions such as canopy size, ground clearance and fascia height, support column dimensions and locations, fuel dispensing module locations and drains. Photographing the canopy from different angles is recommended.

An initial visual inspection is made of the canopy installation taking notes as to the canopy roof, its support structure and drainage, and noting whether the structural steel components are welded or bolted or a combination thereof. A determination is made as to how drainage from the roof is handled. The visual inspection includes a physical examination of the base of each support column, the top of each support column, all visible drains and the top of the canopy, observing the condition of the gutters, namely whether they are rusty or clogged with debris; and whether or not the discharges from the gutters to the support columns are clogged.

The method of inspecting canopies may include an impact and resonance test procedure following the visual inspection of the columns for holes, rust, and loose or defective paint. An initial impact test is conducted using an impact tool such as a ball and peen hammer. Each column is struck with the tool, as if driving a nail, at about the ear level of a person standing and doing the testing or at about four or five feet above the base of the column. A record is made of the impact test. Was it destructive? Was the sound a hollow or solid sound? Was there a sound of falling debris? If the initial test does not produce a destructive result, the impact test is repeated on the opposite side of the column at a height of about two feet below the initial test or at a height intermediate the lower end of the column and the height of the initial test.

Figure 13:
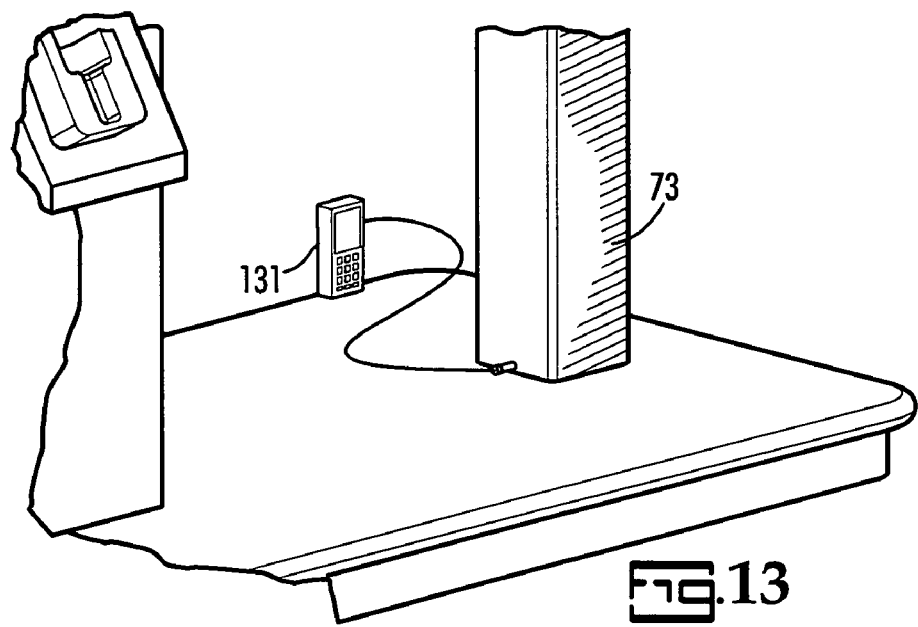
FIG. 13 shows testing the lower end of a support column with an ultrasonic thickness gauge.
Figure 14:
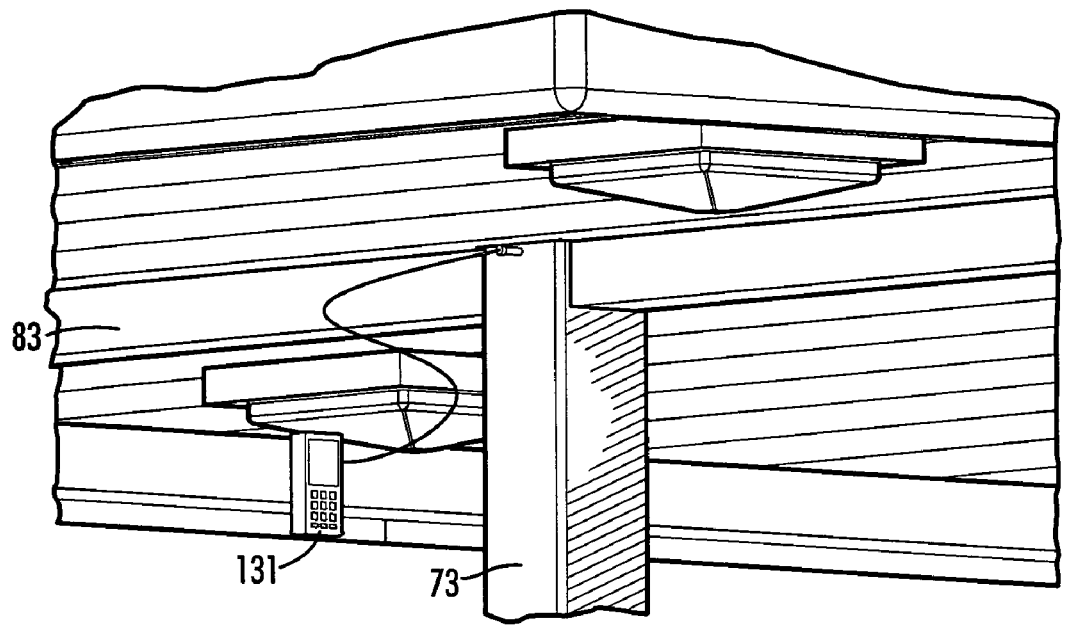
FIG. 14 shows measurement of the support column wall thickness at the underside of the roof with an ultrasonic thickness gauge.
Figure 15:
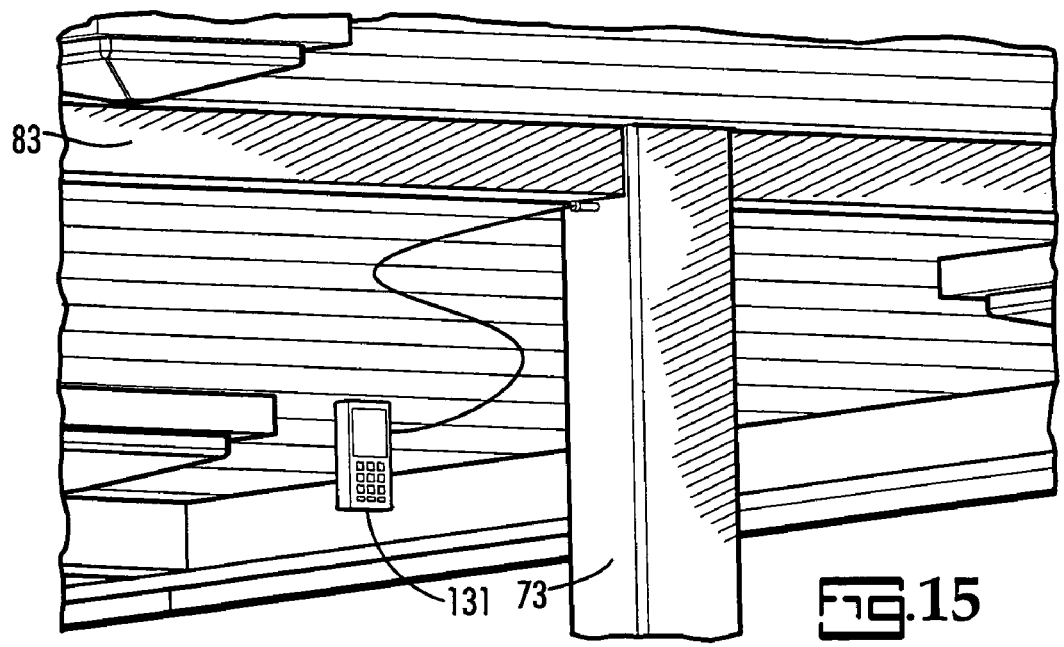
FIG. 15 shows measurement of the support column wall thickness at its junction with a laterally extending gutter.

It is preferred that the support columns be tested for wall thickness with ultrasonic testing equipment, after calibrating the thickness gauge of the ultrasound testing equipment. The column thickness readings at all four sides at the base of each column are recorded. If a thickness reading is not obtained near the bottom, the sensor is moved vertically up the column until a reading is obtained and the height at which the reading is obtained and its value are recorded. The last mentioned column thickness test procedure is preferably preformed on all four sides of the column at its top. It is also desirable that a recorded top to bottom scan of all four sides of each column be made producing graphs showing deviations in wall thickness. This is done using the scan mode of the thickness gauge of the ultrasonic testing equipment. The graph on the thickness gauge display is recorded by an image recording device or photographed and referenced as to location on the support column. This definitative examination is essential for an engineering analysis in evaluating the risk of a canopy collapse. FIG. 13 shows an ultrasonic thickness gauge 131 being used measuring the thickness of the column wall at one side of the support column 73 near its bottom. FIG. 14 shows an ultrasonic thickness gauge 131 being used to measure the thickness of the wall of the column 73 near its upper end and FIG. 15 shows the ultrasonic thickness gauge being used to measure the adjacent wall of the support column 73 just below the junction of the gutter 83 with the support column 73.

Figure 16:
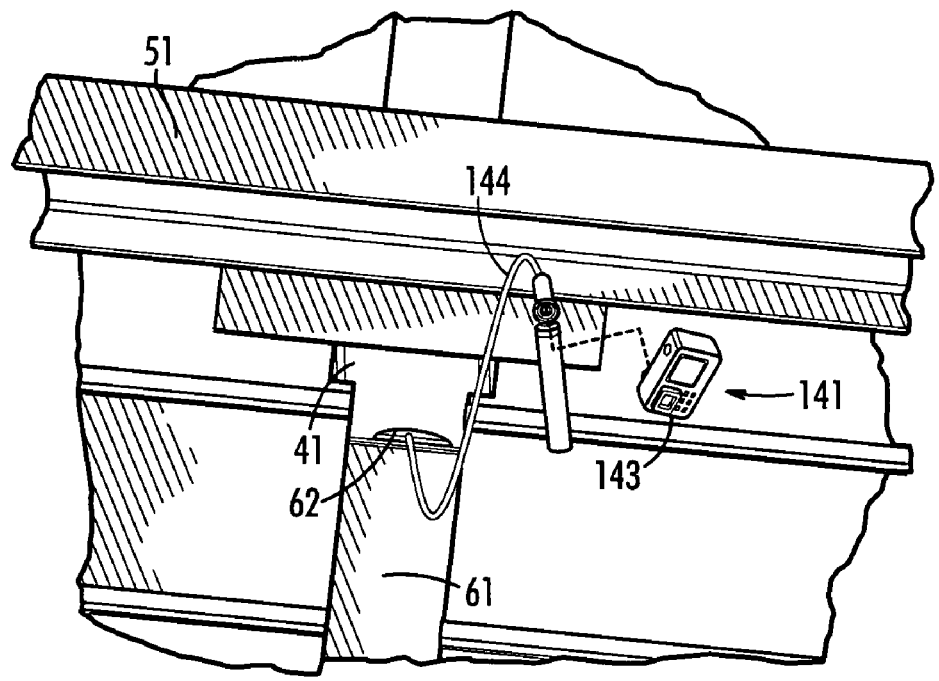
FIG. 16 shows a fiber scope with an attached digital camera taking pictures of the interior of the upper end of a canopy support column.
Figure 17:
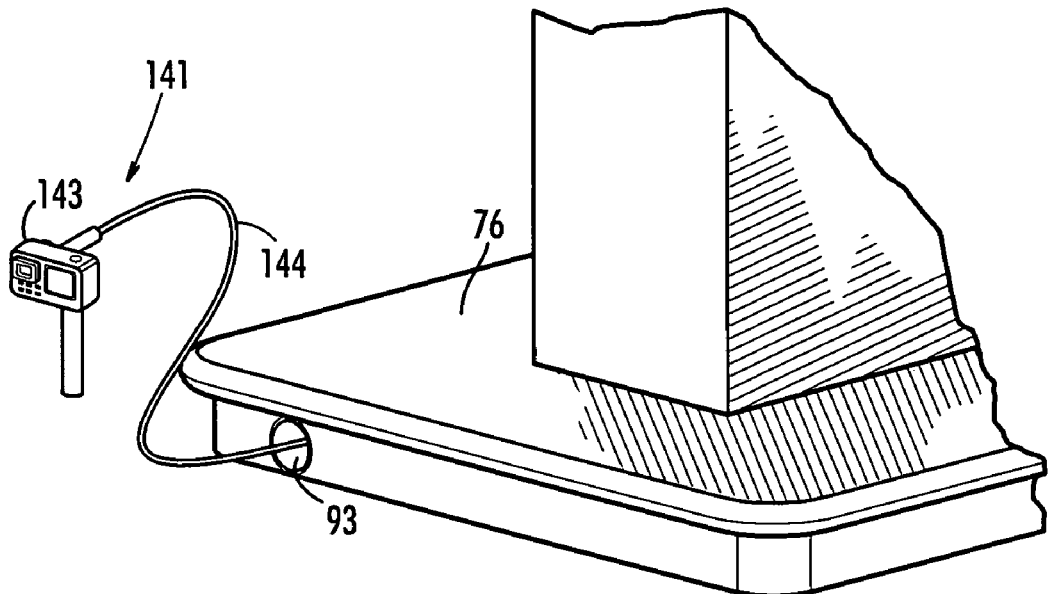
FIG. 17 shows a fiber optic scope with digital camera taking pictures of the interior of a drain in fuel dispending island.

As shown in FIG. 16 a fiberscope testing device or equipment 141 is being used to observe, through opening 62, the interior of the upper end of the hollow support column 61 and, as shown in FIG. 17, the fiberscope testing equipment 141 is used to view the inside of the column drain 93 passing through the island 76. This allows the people performing the inspection to observe and record the nature of any clogged condition of the inspected components of the canopy drainage system. The fiberscope testing equipment includes a camera or image recording device 143 for recording images or pictures which are included in the written report of the inspection. It may be desirable to drill small diameter holes in the support columns in order to insert the fiber bungle or probe 144 into the interior of the vertical support columns, thereby permitting the inspector to view and record images of selected areas of the interior of the columns.

Figure 18:
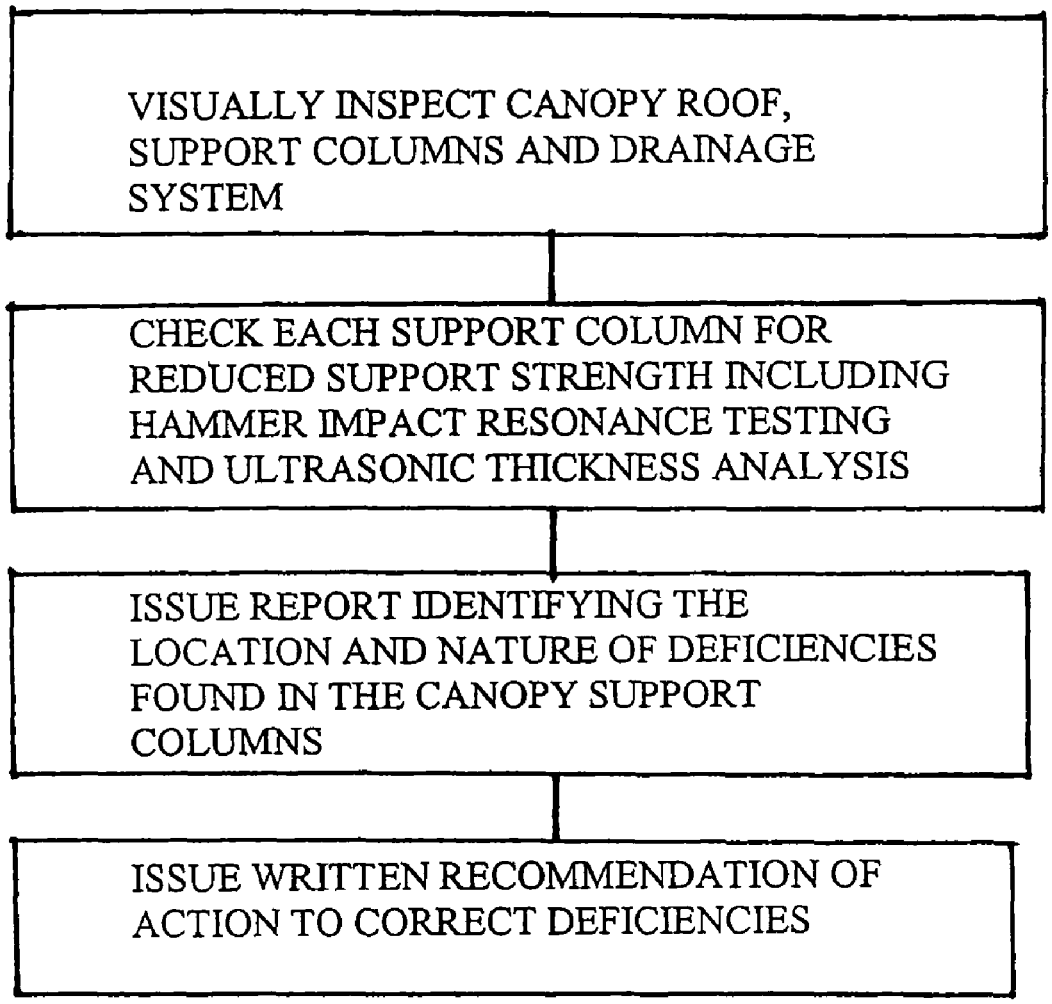
FIG. 18 through 22 illustrate some of the herein disclosed methods of inspection.
Figure 19:
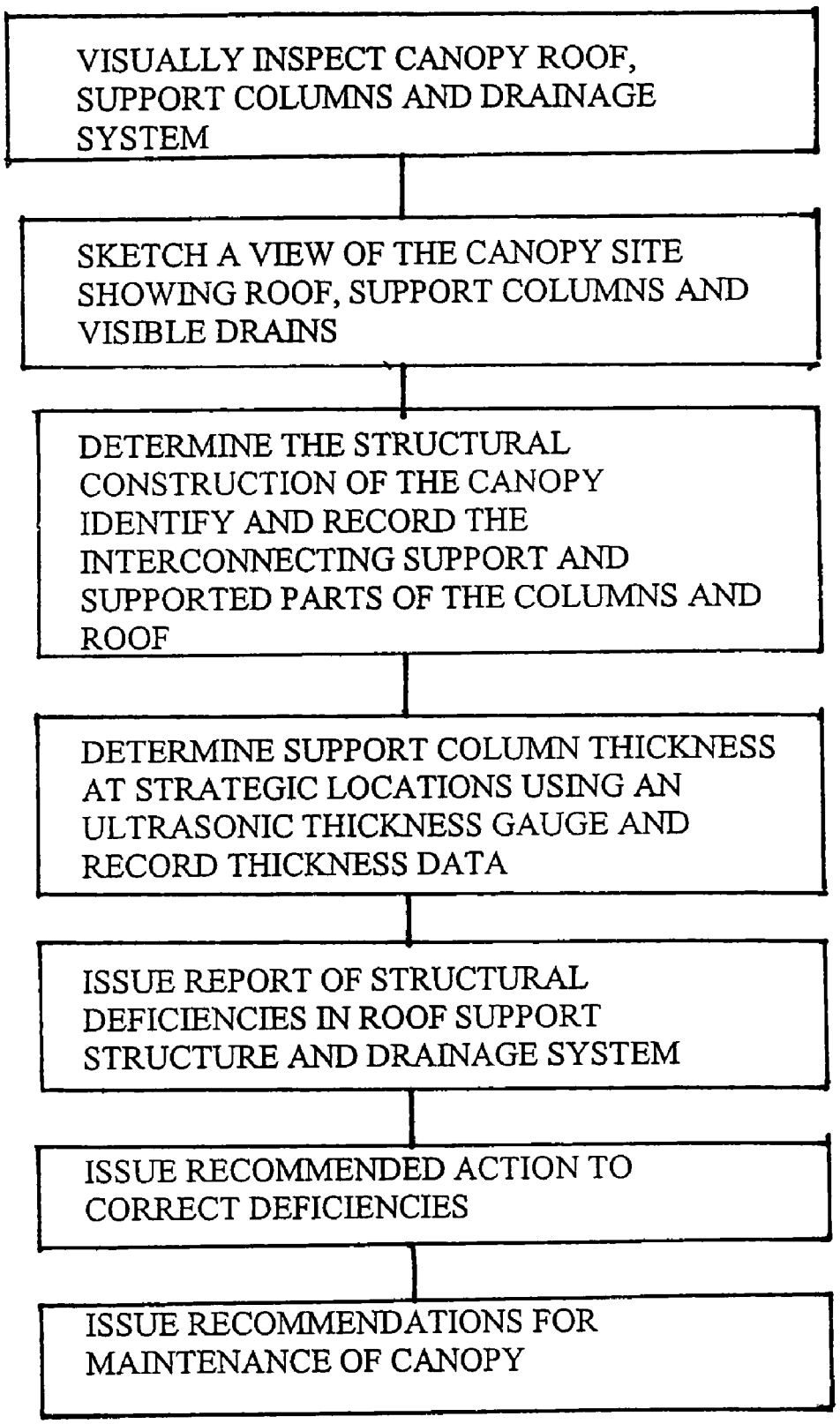
Figure 20:
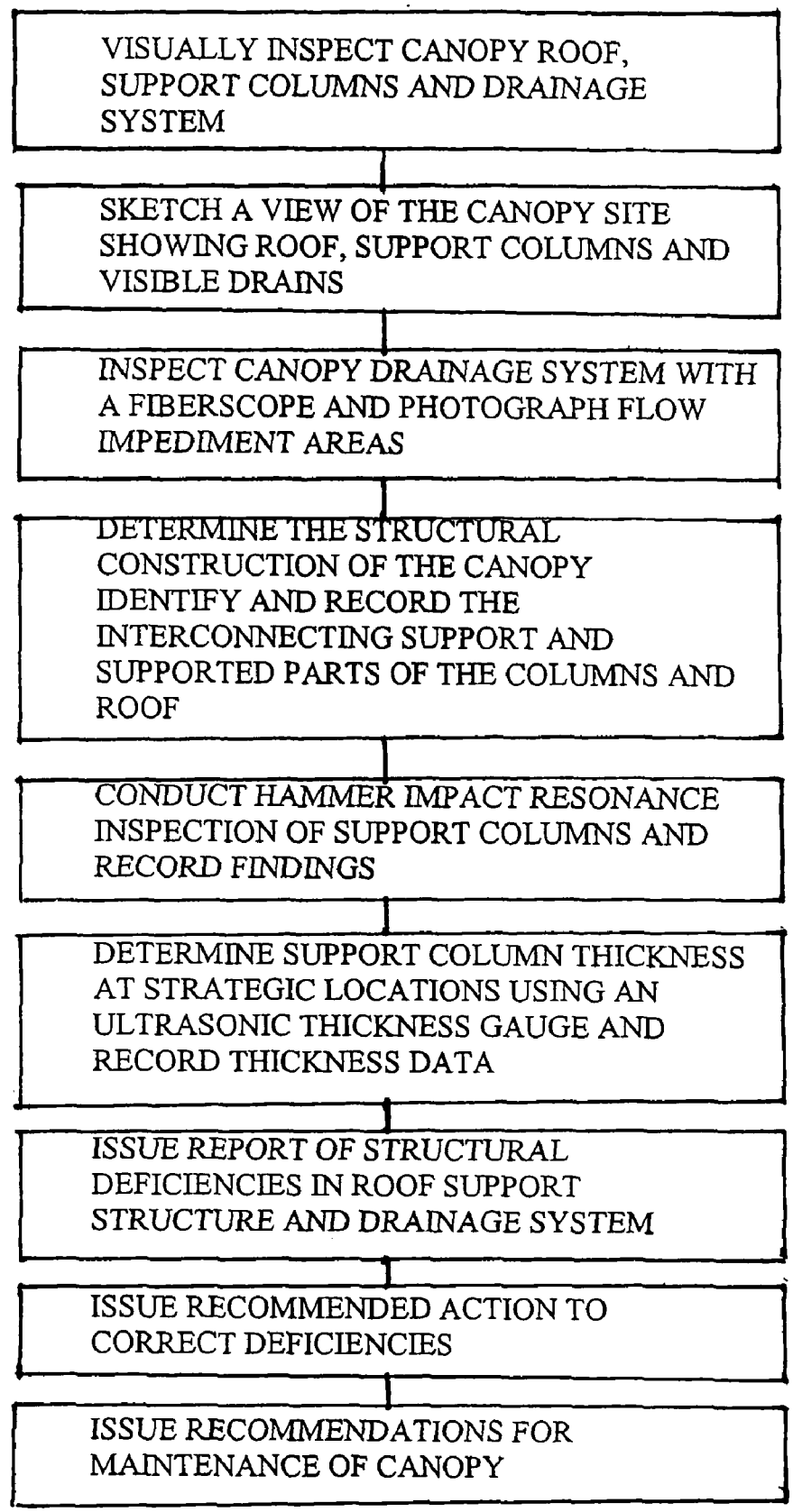
Figure 21:
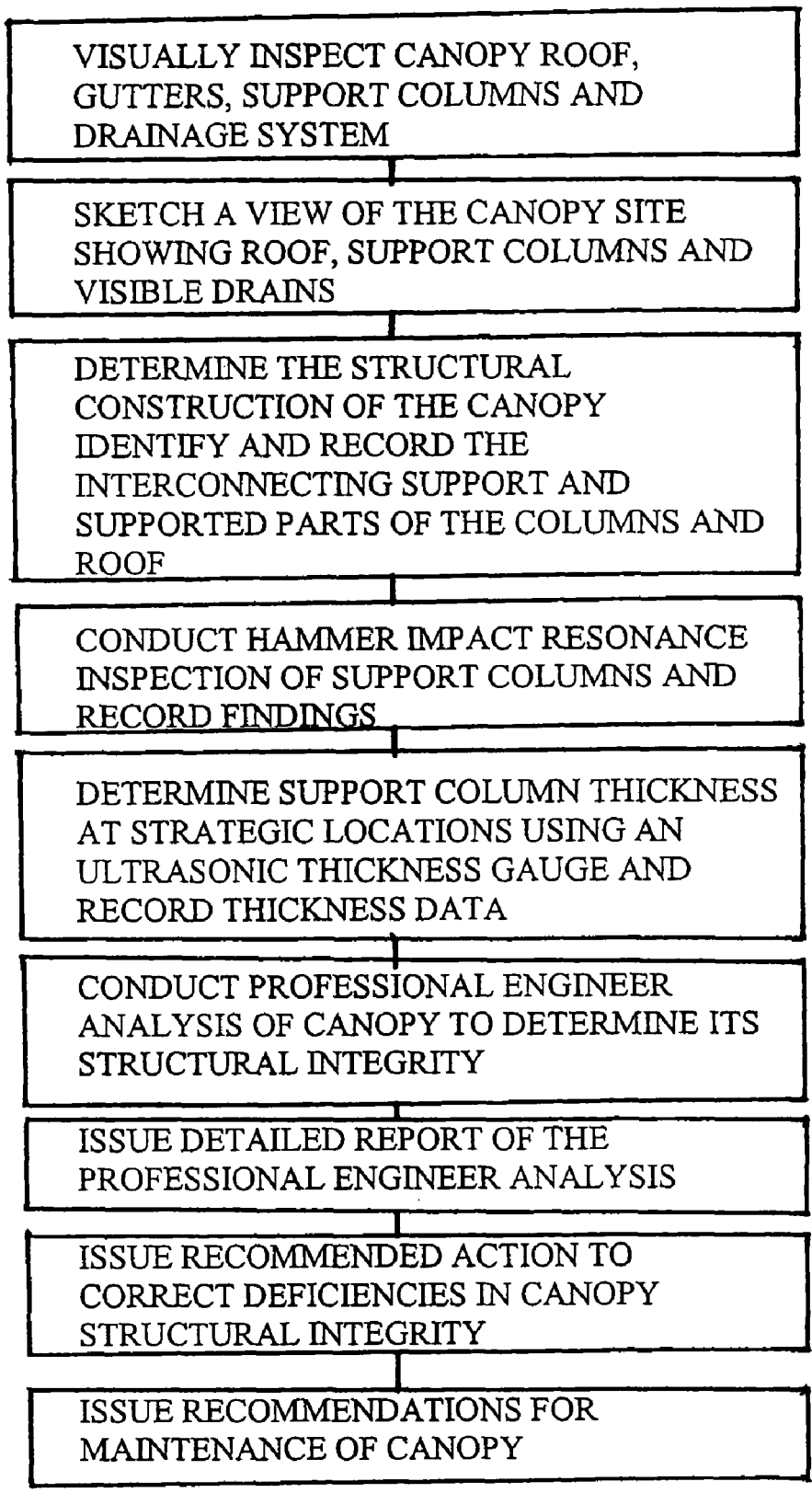
Figure 22:
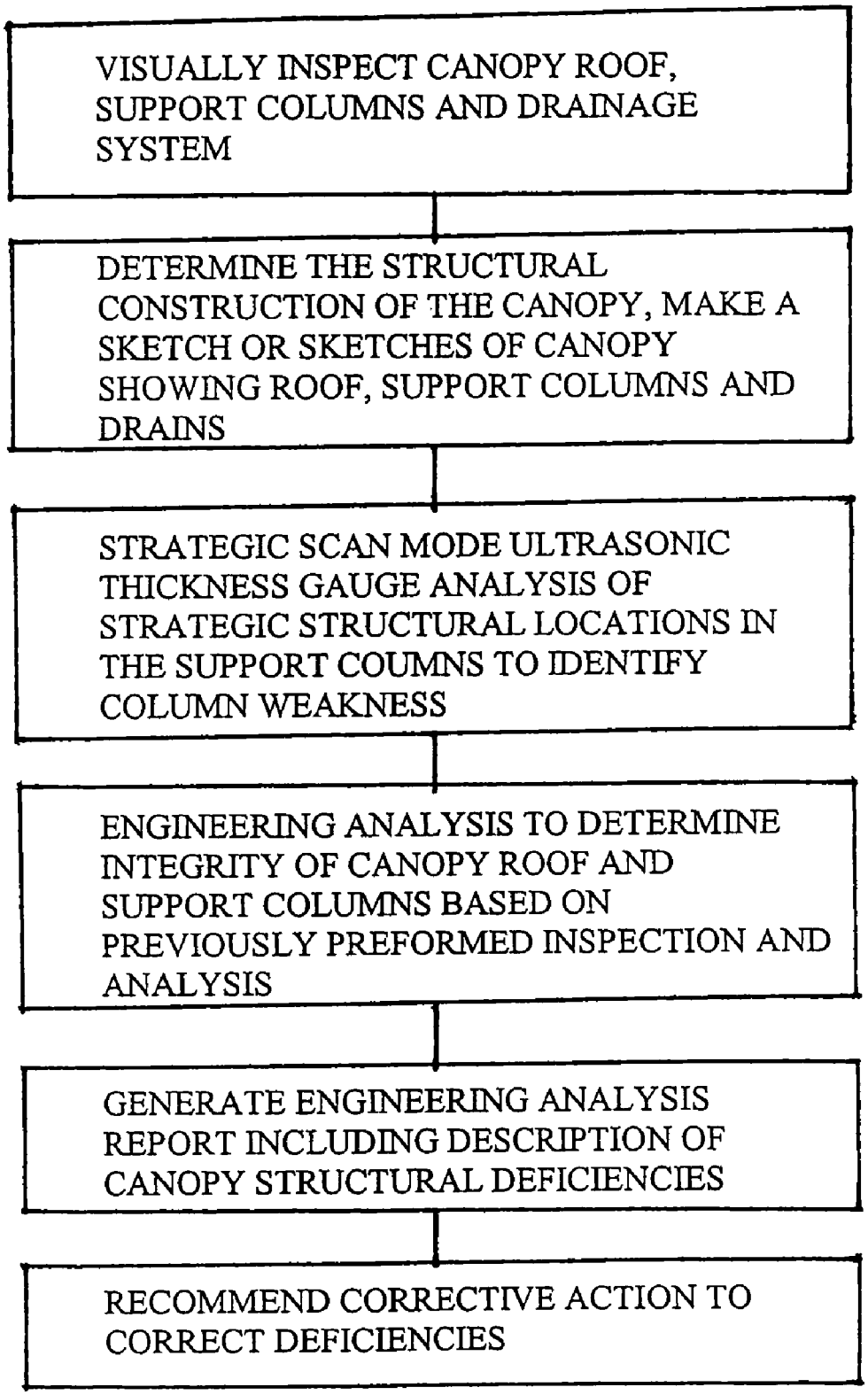

The scope of the canopy inspection is decided by the owner of the canopy and an appropriate plan or method of inspection is chosen to determine the integrity of the canopy support system. Each inspection plan includes a report of findings and recommendations of corrective action to remedy apparent or discovered deficiencies. If there is no apparent deterioration of the canopy support system a limited somewhat cursory plan of inspection may be chosen. One such cursory canopy inspection is performed by the method shown in FIG. 18 which includes the step of visually inspecting the canopy to identify areas of deterioration or concern and recording the location and nature of the deterioration. A cursory inspection includes ultrasonic testing of the thickness of the walls of the support column. The cursory inspection method also includes the steps of issuing a written report identifying the location and nature of the deficiencies in the canopy support system uncovered by the foregoing steps and issuing written recommendations as to corrective action to correct or remedy the deficiencies. The foregoing cursory inspection method may include issuance of written recommendations for maintenance of the canopy.

As illustrated in FIGS. 19 through 22, more comprehensive methods of inspection of the canopy can be performed to more precisely identify and evaluate parts of the support structure weakened by corrosion. A strategic scan mode ultrasonic thickness gauge analysis of strategic structural locations of the canopy is preferably included to identify flaws or defects at critical construction points such as at the bases of the support column and at the connections between the top of the support columns and the roof stringers or support beams. A top to bottom scan of laterally opposite sides, or all four sides, of each column to produce recorded graphs of wall thickness should also be conducted to provide data for a structural analysis of each column. An engineering analysis is conducted to determine the integrity of the existing canopy support structure based on structural characteristic found from the inspection with due regard for current applicable design techniques and requirements. In addition to such an engineering analysis, written recommendations for correction of deficiencies in the support structure are rendered.

The drainage of water from the roof through the hollow support columns provides the moisture conducive to rusting or corrosion of the inside of the hollow steel support columns. The method of inspection includes a visual inspection of the roof drainage system and, preferably, also includes fiberscope inspection with attendant image recordation, particularly images of stoppages, debris and areas of leakage. The inspection report includes a description of the drainage investigation, together with prints of recorded images.

The herein disclosed methods of inspecting canopies are designed to greatly reduce the risk of collapse of the canopy by providing timely information concerning possible deterioration in the canopy support structure. Each method of inspection preferably includes reporting the results of the inspection and recommendations for action to correct deficiencies in the support system revealed from the inspection. The reduced risk of canopy collapse, and probable reduction in insurance premiums, makes the inspection cost effective.

What is claimed is:

1. A method of inspecting a canopy structure having a roof and a plurality of hollow vertical support columns, comprising the steps of:
    inspecting the drainage from the roof to determine whether or not the roof drainage is through the hollow support columns using a fiberscope having a probe,
    if drainage is through the support columns determining where the drainage exits the support columns,
    conducting an ultrasonic thickness inspection of at least upper and lower ends of each column,
    determining wall thickness of said support columns using an ultrasonic thickness gauge equipped with a scanner and a display screen,
    scanning said support columns with said gauge,
    displaying a profile of said wall thickness on said screen, and
    issuing a written report detailing findings of the foregoing steps by including images of said profile displayed on said screen.

2. The method of claim 1 including conducting an impact and resonance test which includes striking one side of each column with an impact tool at approximately ear level of a person conducting said test and noting whether or not there occurs a solid sound or a hollow sound, whether or not there occurs a sound of falling debris and whether or not a hole or a crack develops from said striking of said column.

3. The method of claim 2 wherein said impact and resonance test is also performed by striking each column on its opposite side at a height intermediate said ear level and the lower end of said column.

4. The method of claim 1, further comprising the step of conducting a professional engineer analysis of the structural integrity of the support columns.

5. The method of claim 1, further comprising the step of determining whether the drainage is through piping installed within the columns, if drainage is through the support columns.

6. The method as recited in claim 1, wherein laterally opposite sides of said support columns are scanned from end to end in said scanning step.

7. A method of inspecting a canopy structure having a roof and a plurality of hollow vertical support columns, comprising the steps of:
    inspecting the drainage from the roof to determine whether or not the roof drainage is through hollow support columns using a fiberscope having a probe wherein said fiberscope includes an image recording device and wherein said step of inspecting said drainage system includes recording images;
    if drainage is through the support columns, determining where drainage exits the support columns;
    conducting an ultrasonic thickness inspection of at least the upper and lower ends of each column;
    determining wall thickness of said support columns using an ultrasonic thickness gauge equipped with a scanner and a display screen,
    scanning said support columns with said gauge,
    displaying a profile of said wall thickness on said screen, and
    issuing a written report detailing findings of the foregoing steps by including images of said profile displayed on said screen.

8. The method of claim 7, further including the step of conducting an impact and resonance test which includes the steps of:
    striking one side of each column with an impact tool at approximately ear level of a person conducting said test; and
    noting whether there occurs a solid sound or a hollow sound, whether or not there occurs a sound of falling debris and whether or not a hole or a crack develops from said striking of said column.

9. The method of claim 8 wherein said impact and resonance test conducting steps also include the step of striking each column on its opposite side at a height intermediate said ear level and the lower end of said column.

10. The method of claim 7 wherein said inspecting step further comprises the steps of
    making a hole in each column near each of its top and bottom ends;
    selectively inserting said probe through said holes;
    inspecting the interior of each column for obstructions to drainage; and
    recording images of the interior of each column.

11. A method of inspecting a canopy structure having a roof and a plurality of hollow vertical support columns, comprising the steps of:
    inspecting the drainage from the roof to determine whether or not the roof drainage is through hollow support columns using a fiberscope having a probe by
        making a hole in each column near each of its top and bottom ends,
        selectively inserting said probe through said holes,
        inspecting the interior of each column for obstructions to drainage, and
        recording images of the interior of each column;
    if drainage is through the support columns, determining where drainage exits the support columns, and conducting an ultrasonic thickness inspection of at least the upper and lower ends of each column;

determining wall thickness of said support columns using an ultrasonic thickness gauge equipped with a scanner and a display screen, scanning said support columns with said gauge, displaying a profile of said wall thickness on said screen, and issuing a written report detailing findings of the foregoing steps by including images of said profile displayed on said screen.

12. The method of claim 11 including conducting an impact and resonance test which includes the steps of:

striking one side of each column with an impact tool at approximately ear level of a person conducting said test; and noting whether or not there occurs a solid sound or a hollow sound, whether or not there occurs a sound of falling debris and whether or not a hole or crack develops from said striking of said column.

13. The method of claim 12 wherein said impact and resonance test conducting step includes the step of striking each column on its opposite side at a height intermediate said ear level and the lower end of said column.

14. The method of claim 11, further comprising the step of producing illustrations of the canopy structure showing the roof, the vertical support columns, gutters and system of drainage from the roof.

15. The method of claim 11, further comprising the step of issuing a recommendation of action to correct deficiencies in structural integrity of the support columns.

* * * * *